(12) United States Patent
Rothe et al.

(10) Patent No.: US 7,341,604 B2
(45) Date of Patent: Mar. 11, 2008

(54) HIGHLY AFFINE COSMETIC AGENT

(75) Inventors: Helga Rothe, Darmstadt (DE); Pierre Aeby, Marly (CH); Otto Goettel, Marly (CH); Hans-Juergen Braun, Ueberstorf (CH)

(73) Assignee: Wella AG, Darmstadt (DE)

( * ) Notice: Subject to any disclaimer, the term of this patent is extended or adjusted under 35 U.S.C. 154(b) by 326 days.

(21) Appl. No.: 10/511,671

(22) PCT Filed: May 12, 2003

(86) PCT No.: PCT/EP03/05021

§ 371 (c)(1),
(2), (4) Date: Oct. 18, 2004

(87) PCT Pub. No.: WO04/000257

PCT Pub. Date: Dec. 31, 2003

(65) Prior Publication Data

US 2006/0174423 A1   Aug. 10, 2006

(30) Foreign Application Priority Data

Jun. 19, 2002  (DE) ............................ 102 27 238

(51) Int. Cl.
*A61K 7/13* (2006.01)
(52) U.S. Cl. .................. 8/405; 8/552; 8/563; 132/202; 132/208; 424/70.1; 424/70.6
(58) Field of Classification Search .............. 8/405, 8/552, 563; 132/202, 208; 424/70.1, 70.6
See application file for complete search history.

(56) References Cited

U.S. PATENT DOCUMENTS 6,537,330 B1   3/2003   Hoeffkes et al.

2003/0131425 A1   7/2003   Hoeffkes et al.

FOREIGN PATENT DOCUMENTS

| DE | 43 35 628 | | 4/1995 |
|---|---|---|---|
| JP | 2003-104847 | * | 4/2003 |
| WO | 99/33901 | | 8/1998 |
| WO | 99/66890 | | 12/1999 |
| WO | 02/29407 | | 4/2002 |
| WO | WO 02/29407 A1 | * | 4/2002 |

OTHER PUBLICATIONS

STIC Search Report Dated, Oct. 30, 2006.*
English translation of the Japanese Patent 2003-1048477.*
STIC Search Report dated Jun. 20, 2007.*
James J. Delvin, et al: "Random Peptide Libraries . . . " Science, Jul. 1990, pp. 249, 404-406.

* cited by examiner

*Primary Examiner*—Eisa Elhilo
(74) *Attorney, Agent, or Firm*—Michael J. Striker

(57) ABSTRACT

The cosmetic composition for cosmetically treating parts of the body comprising keratin-containing material includes one or more conventional cosmetic auxiliary ingredients and a cosmetically active compound, which is prepared by covalently bonding peptide linker molecules with known organic cosmetic effector molecules. The peptidic linker group is a peptide group, preferably with from 2 to 15 amino acids, which has binding specificity for keratin-containing material. The organic cosmetic effector molecules have dyeing, care-imparting, conditioning, protective, hardening, softening, repairing and/or strengthening properties for keratin-containing material. The method of cosmetically treating parts of the body that include keratin-containing material, for example a method of dyeing hair, includes applying the above-described cosmetic composition to the parts of the body.

21 Claims, No Drawings

HIGHLY AFFINE COSMETIC AGENT

CROSS-REFERENCE

This is the U.S. National Stage of PCT/EP 03/05021, filed May 14, 2003, which, in turn, claims the benefit of priority of invention based on DE 102 27 238.7, filed Jun. 19, 2002 in Germany.

BACKGROUND OF THE INVENTION

The subject matter of the present invention includes cosmetic agents comprising two components covalently linked to each other and having functions that differ from one another, the first component being a peptidic linker molecule with high affinity or binding specificity for keratin-containing material and the second component being at least one cosmetic agent consisting of at least one cosmetically active compound known per se or a cosmetic effector molecule for the cosmetic treatment of keratin-containing material.

The combination of the invention finds general use in the cosmetic treatment of parts of the human or animal body that contain keratin and particularly as a hair-treating agent.

The targeted and in terms of quantity and method optimum use of cosmetic products is based on the idea of being able to apply the agents or materials in question in as efficient a manner as possible to the desired parts of the body and to exclude as much as possible other areas of the body.

To achieve this goal, three methods are available in principle. According to one method, the cosmetic agent exhibiting the desired action can be applied to the desired body site locally by means of appropriate mechanical aids, while at the same time covering the body areas with which the cosmetic agent in question is not to come in contact. This method, however, has the drawback that it allows one to reach only the directly accessible parts of the body, that contact with undesirable body sites can practically be difficult to avoid and that the handling of the method is awkward.

According to the second method, it is possible, based on certain chemical and biochemical/physiological properties, to select cosmetic agents that preferentially bind or adhere to certain structures (for example skin, hair, nails). The drawback of these methods is, in particular, that the use of these substances is highly restricted by their chemical nature so that the desired site-specific action of the cosmetic agent in question often does not occur in the hoped-for manner and that the material is not suited for cosmetic use.

As a third possibility, it has recently been proposed to use various antibodies with different specificity for cosmetic agents as vehicles for a targeted application of cosmetic agents. In this manner, by coupling with antibodies, the cosmetic agents are transported to the desired sites.

Such methods have, in particular, the drawback that the preparation of the antibodies is very expensive and that antibodies are relatively large, complicated and biologically active protein units the use of which, as is known, is not without problems from both a biochemical and a physiological standpoint.

SUMMARY OF THE INVENTION

The object of the present invention is to provide cosmetic agents and novel methods for cosmetic treatment that eliminate the drawbacks of the prior art.

This object is attained by providing a high-affinity cosmetic agent comprising two components that are covalently linked to each other and have functions that differ from one another, the first component being a peptidic linker molecule with high affinity or binding specificity for keratin-containing material, and the second component being at least one cosmetic agent consisting of at least one known organic cosmetically active compound or an organic cosmetically active effector molecule.

Surprisingly, we have now found that peptides with a chain length of between 2 and 30 amino acids, preferably between 6 and 15 amino acids and particularly between 6 and 12 amino acids, on the one hand, can bind specifically to keratin-containing material, particularly hair, and, on the other, can be linked with cosmetically active compounds in a manner such that with the said peptidic linker molecule the cosmetically active compound in question can be applied in advantageous manner to a keratin-containing material (particularly hair)

In this manner a cosmetic agent is obtained which consists of two components covalently linked to each other, namely a peptidic linker molecule with binding specificity for keratin or keratin-containing material, and at least one cosmetic agent bound thereto. The peptidic linker molecule acts as a binding agent and vehicle for the cosmetically active compound, it being possible for several cosmetically active compounds to be linked to the same peptidic linker. A cosmetic agent with high affinity for the keratin-containing material, particularly for animal and human hair, is obtained in this manner.

Another object of the present invention is the use of the cosmetic agent in question for cosmetic treatment of keratin-containing material and the use of the peptidic linker molecule in question and of the effector molecules for the preparation of a cosmetic agent with high affinity or binding specificity for keratin or keratin-containing material.

The cosmetic agent according to the present invention has numerous advantages. Particularly noteworthy among these is the targeted use of cosmetic agents (dyes, cosmetic care agents, conditioners) so that these agents can exert their action essentially only at certain desired sites of the body, particularly on hair. Moreover, in this manner it is possible to achieve a stronger and longer-lasting hold of the cosmetic agent at the application site, particularly hair, so that, depending also on the binding strength of the peptidic linker molecule, a controllable or controlled retention time or intensity of the cosmetic agent, for example a dye, can be attained. A lower quantitative consumption of the cosmetic agent in question can be pointed out as an additional advantage.

Moreover, with the cosmetic agent of the present invention, several advantageous properties can be combined in one and the same product. For example, an effector molecule with hair-care action can, via the peptidic linker, be linked with a hair dye molecule giving rise to a product that at the same time is a hair-care product and a hair colorant.

Also, the peptidic linker itself can have cosmetic care properties so that with even just a single binding, for example, of a color-producing effector molecule to a peptidic linker, it is possible to obtain products that at same time are cosmetic care-imparting products and colorants. Thus, the cosmetic agent of the invention can exhibit at least two different cosmetic actions.

Another advantage of the cosmetic agent of the invention is its very high variability which can also be controllable. For example, different peptidic linkers with different binding strengths for keratin-containing material can be linked with entirely different effector molecules, for example a surface-active substance and a hair dye. In this case, a cosmetic agent is provided in which the effector molecules, through the different binding properties of "their" peptidic linkers, can provide an individual retention time or individual properties at the site of application.

Furthermore, hair damaged by mechanical action (for example combing or rubbing), chemical action (for example dyeing, bleaching, waving, defrizzing) or physical action (UV radiation, weathering effects) can, compared to healthy hair, show different binding strengths and binding sites for the peptidic linker. In such cases, a cosmetic agent of the invention can bind preferentially to damaged areas of the hair, for example hair tips damaged by splicing, because the peptidic linker molecule binds preferentially and unusually strongly with a cosmetic-care effector molecule and/or a coloring effector molecule and/or an effector molecule acting as a UV filter.

From this, a person skilled in the art can clearly see the possibilities offered by the present invention of providing numerous cosmetic agents with advantageously combined properties.

By "keratin-containing material" are meant for purposes of the present invention the skin and skin appendages, for example scalp hair, eyebrows, eyelashes, toenails and fingernails of the animal and human body.

By "peptidic linker molecule" are meant for purposes of the present invention polymers the monomers of which are amino acids connected to each other by the usual acid amide bonds. Said polymers can be of synthetic (prepared by total industrial synthesis), semisynthetic (obtained by partial synthesis and from natural sources) or natural origin, methods of preparation involving genetic engineering (for example the known methods of DNA recombination, phage-peptide libraries or phage display) being included. Suitable amino acids are both the L-and the D-amino acids as well as the amino acids modified by, for example, glycosylation (by methods that in themselves are known).

By "cosmetic agents" or "cosmetically active compounds" or "cosmetic effector molecules" are meant compounds, substances or molecules which are known to exert a cosmetic action on the surface of the animal or human body, particularly those with dyeing or coloring, cosmetic care-imparting, conditioning, protective, hardening, softening, repairing and/or reconstituting properties. In the following, the term "effector molecule" is used as a synonym for "cosmetic agent" or "cosmetically active agent".

Thus, the present invention includes the use of a peptidic linker molecule and at least one organic cosmetically active effector molecule with dyeing or coloring, cosmetic care-imparting, conditioning, protective, hardening, softening, repairing and/or reconstituting property for preparing a cosmetic agent.

The coupling of a peptidic linker molecule with an effector molecule can be achieved by known chemical methods.

DESCRIPTION OF THE PREFERRED EMBODIMENTS

Preferred peptidic linker molecules are glycine or glycine derivatives which for binding to effector molecules contain appropriate heteroatoms or heteroatom groupings. Suitable glycine derivatives are the alpha-amino acids with at least three carbon atoms, the suitable heteroatoms or heteroatom groups, for example an amino, hydroxyl, sulfonyl or carboxyl group, preferably being attached to the terminal carbon atom.

Suitable effector molecules are preferably dyes or dye precursors containing a reactive group capable of forming a covalent bond with the heteroatoms or heteroatom groups.

Suitable reactive groups are, for example, the triazinyl, sulfatoethoxysulfonyl or vinylsulfonyl groups. It is also possible, however, to use as the reactive groups halopyrimidine, chloracetamide, carbamate, epoxide or methylol groups.

Suitable dye precursors are, for example, halonitroaromatic compounds such as 2,4-dinitrofluorobenzene, 2,6-dinitrofluorobenzene or 4-fluoro-3-nitroaniline.

The coupling reaction of an effector molecule can take place, for example, according to the following scheme. In this case which is used as an example, the effector molecule is a dye or dye precursor.

According to the following reaction scheme, glycine derivatives of formula I can be condensed with dyes or dye precursors $R_F$-Y containing an appropriate reactive group to give dyes of formula II;

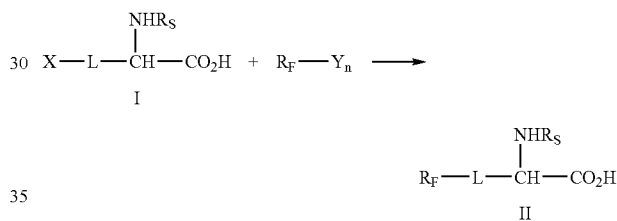

wherein $R_F$ denotes a dye or dye precursor, $R_S$ denotes a hydrogen atom or a t-butoxycarbonyl (Boc) group, L denotes an alkylene group or phenylene group and X denotes an amino, hydroxyl or sulfonyl group, and Y is selected from among a halogen atom (F, Cl, Br) or one of the following atomic groupings:

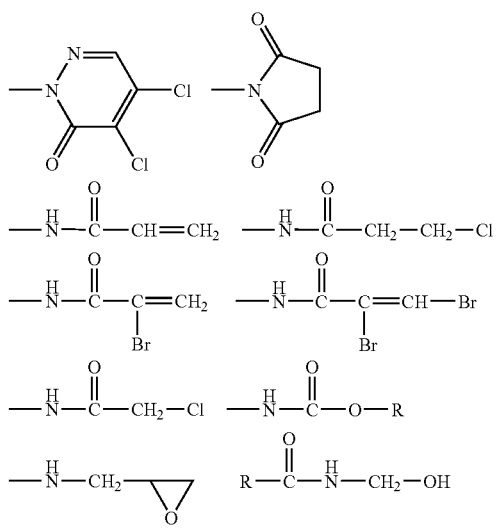

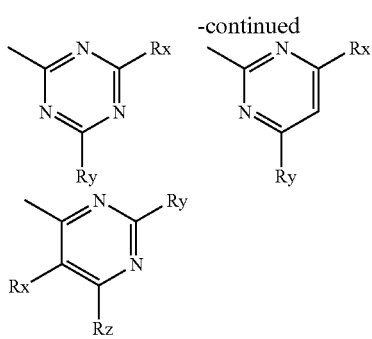

wherein $R_x$, $R_y$ and $R_z$ independently of each other denote F, Cl, Br or an NR1R2 group, an OR1 or an SR1 group, provided that R1 and R2 independently of each other stand for a hydrogen atom, a straight-chain or branched $C_1$-$C_6$-alkyl group, an aromatic or heteroaromatic ring with 5-6 ring atoms or a totally or partly saturated ring compound with 5 to 7 ring atoms.

Suitable derivatives of the amino acids of formula I are preferably compounds containing a free amino, hydroxyl or sulfonyl group, for example the derivatives of 3-aminoalanine, ornithine, lysine, serine, threonine, cysteine and homocysteine.

The finding and selecting of a peptidic linker molecule with binding specificity for keratin-containing material suitable for the purpose of the present invention can be accomplished by known methods and is trivial for a person skilled in the art.

The peptidic linkers and masked amino acids suitable for the present invention can be prepared by known methods or obtained commercially, for example from ORPEGEN Pharma, Heidelberg. For example, a peptide of the desired chain length of, for example, 10 amino acids can be synthesized by routine methods, for example by the generally known Merrifield technique.

The choice of amino acids that are suitable for the synthesis of the peptide preferably depends on their charges or on the arrangement of charged side groups and/or of amino acid side groups capable of forming hydrogen bonds. Among such amino acids can be mentioned, for example, glutamic acid, aspartic acid, arginine, histidine, tyrosine, threonine and lysine.

Moreover, suitable peptides can be identified by the screening of phage peptide libraries (also known as "phage display", for example according to Devlin, J. J. et al., Science 249, 404-406, 1990) and by possible further optimization thereof by the "cosmix-plexing" method according to WO 98/33901.

The peptides that are suitable as peptidic linker molecules and have sufficiently high binding affinity for keratin-containing material can be selected by known methods, for example, by bringing a keratin-containing material, preferably hair, in contact with at least one linker-effector combination according to the present invention. This can be accomplished, for example, by immersing a hair sample into an aqueous solution at room temperature (20 to 22° C.) at a pH in the range from 5 to 6, the solution containing a combination of a peptidic linker and a colored effector molecule (for example, 6-[(4-amino-2-nitrophenyl)amino]-(2S)-2{[(1,1-dimethylmethoxy)carbonyl]amino}hexanoic acid). After an exposure time of about 2 to 10 minutes, the binding of the effector molecule to the hair can then be determined by wash-out tests with a common hair-washing agent (shampoo).

The binding affinity for the keratin-containing material of the peptidic linker molecules that are suitable for the invention is not critical. According to the invention, appropriate are peptidic linkers showing specific binding to keratin-containing material in aqueous solution at a pH in the range from 4.0 to 8.5, preferably from 5.0 to 6.0, and, in comparison with a sample with, for example, a simple hair dye without peptidic linker, withstands at least four common hair washings with a conventional shampoo without an appreciable loss in efficacy.

The higher the affinity of the peptidic linker the stronger is the adherence of the cosmetic agent in question to the desired site of application.

By selecting the peptidic linker according to its affinity for keratin or keratin-containing material, the cosmetic agent in question will adhere to the site of application more or less strongly so that with the present invention the effector molecules in question can be bonded with varying strength, fastness or permanence. It is thus possible to prepare cosmetic agents which in terms of retention time are quite differently adapted to the individual requirements.

As already stated, the term effector molecule includes substances that exert a cosmetic action on the surface of an animal or human body, particularly substances with dyeing or coloring, cosmetic care-imparting, conditioning, protective, hardening, softening, repairing and/or reconstituting properties.

Suitable effector molecules for the present invention are mainly cosmetic-care providing and/or conditioning and/or protective substances which on the skin or body appendages, particularly hair, are known to be able to exert hardening, softening, repairing or reconstituting activity.

Included are, for example, combability improvers, for example cationic polymers (for example Iniquat FC 370, Jaguar C-162, Polymer JR 125), protein hydrolyzates (for example from wheat), cationic surfactants (for example cetyltrimethylammonium chloride, distearylammonium chloride), amidoamines, betaine esters, ester quats; luster-imparting agents, for example silicon polyols and fatty alcohols, volume providers, for example chitosan; humectants, for example lactates (for example cetyl lactate), vitamins and provitamins or vitamin precursors, for example panthenol, and derivatives thereof, biotin, tocopherols, springiness improvers, for example betaine and derivatives thereof, sugars, for example polysaccharides, oligosaccharides, glucose, fructose or inuline; organic-chemical UV filters including all known UVA- UVB- and UVA/UVB filter substances alone or combinations with one another, for example the derivatives of dibenzoylmethane (for example Parsol 1789 supplied by Givaudan/Roure, INCI name: butyl methoxydibenzoylmethane, benzylidenecamphor or derivatives thereof, particularly methylbenzylidenecamphor (for example 3-benzylidenecamphor, 3-(4-methylenebenzylidene)-d,l-camphor), and derivatives and esters of cinnamic acid, particularly derivatives and esters of methoxycinnamic acid (for example octyl 4-methoxycinnamate or isopentyl 4-methoxycinnamate), derivatives and esters of benzoic acid, particularly of 4-aminobenzoic acids, polyhydroxybenzoic acids (for example methyl polyhydroxybenzoate or propyl polyhydroxybenzoate), esters of salicylic acid (for example 2-ethylhexyl salicylate or 4-isopropylbenzyl salicylate), sulfonic acids, benzophenone and derivatives thereof, for example the sulfonic acid derivatives of benzophenone (for example, 2-hydroxy-4-methoxybenzophenone-5-sulfonic acid) as UVB/UVA filters or of benzimidazoles (for example 2-phenylbenzimidazole-5-sulfonic acid) as well as the salts thereof, dibenzoylmethane or appropriate polypeptides, particularly oxygen radical scavengers, for example the known Mn, Fe or Zn superoxide dismutases, as well as the tocopherols and vitamins (for example ascorbic acid).

The said cosmetic-care and/or conditioning and/or protective effector molecules can be contained in the cosmetic agent of the invention in a total amount from 0.001 to 30.0 wt. %, particularly from 0.01 to 25.0 wt. %, more particularly from 0.1 to 15 wt. % and preferably from 0.5 to 10.0 wt. %, based on the amount of cosmetic agent.

Also suitable are synthetic polymers, particularly acrylic polymers, for example those from the group of crosspolymers of acrylates and alkyl acrylates and/or acrylates and allyl ethers. Suitable for this purpose are, for example, the Pemulen®, Carbopol® and Acrisint® (brands, for example Permulen TR1 supplied by Goodrich (INCI name: Acrylates/C10-30 Alkyl Acrylate Crosspolymer), Carbopol 1382, supplied by Goodrich (INCI name: Acrylates/C 10-30 Alkyl Acrylates Crosspolymer), Carbopol 2984 supplied by Goodrich (INCI name: carbomer) or Carbopol Ultrez 10 supplied by Goodrich (INCI name: carbomer); or Acrisint 400 supplied by 3 V (INCI name: carbomer) which in the cosmetic agents of the invention can be present alone or in combination.

Such polymers can be present in the cosmetic agent in an amount from 0.05 to 5.0 wt. %, particularly from 0.1 to 3.0 wt. % and more particularly from 0.1 to 1.0 wt. %, based on the total amount of the cosmetic agent.

Suitable dyes or coloring effector molecules are all known oxidative, non-oxidative, direct, natural, synthetic or semisynthetic dyes used for the cosmetic dyeing or tinting of keratin-containing materials, particularly hair. Preferred according to the invention are direct dyes. Particularly well suited for this purpose are variously colored nitro dyes, azo dyes, quinone dyes, triphenylmethane dyes and acid and basic dyes.

Also to be mentioned among the suitable dyes are the reactive dyes containing a triazinyl, sulfatoethylsulfonyl or vinylsulfonyl group, for example Reactive Blue 2, Reactive Blue 19, Reactive Red 2, Reactive Orange 16, Reactive Black 5 and Reactive Yellow 2.

Dye precursors can also be used. Suitable dye precursors are, for example, the halonitrobenzene derivatives that can be made to react with compounds having free amino or hydroxyl groups to give nitro dyes. Examples of such dye precursors are 4-fluoro-3-nitroaniline, 5-fluoro-2-nitroaniline, 1-chloro-2,4-dinitrobenzene and 1-fluoro-2,4-dinitrobenzene.

As blue nitro dyes can be mentioned, for example:
1,4-bis[(2'-hydroxyethyl)amino]-2-nitrobenzene,
1,(2'-hydroxyethyl)amino-2-nitro-4-bis-(2"-hydroxyethyl) aminobenzene (HC Blue No. 2),
1-amino-3-methyl-4-(2'-hydroxyethyl)amino-6-nitrobenzene (HC Violet No. 1),
4,N-ethyl,N-(2"-hydroxyethyl)amino-1-(2"-hydroxyethyl) amino-2-nitrobenzene hydrochloride (HC Blue No. 12),
4-bis-(2'-hydroxyethyl)amino-1-(2"-methoxyethyl)amino-2-nitrobenzene (HC Blue No. 11),
1-[(2',3'-dihydroxypropyl)amino]-2-nitro-4-[N-methyl-(2"-hydroxyethyl)amino]benzene hydrochloride (HC Blue No. 10),
1-[(2',3'-dihydroxypropyl)amino]-2-nitro-4-[N-ethyl-(2"-hydroxyethyl)amino]benzene hydrochloride (HC Blue No. 9),
1-(3'-hydroxypropylamino)-2-nitro-4-bis-(2"-hydroxyethylamino)benzene (HC Violet No. 2),
4,N-methyl,N-(2',3'-dihydroxypropyl)amino-1-methylamino-2-nitrobenzene hydrochloride (HC Blue No. 6),
4'-amino-2'-nitro-2"-carboxy-4"-dimethylaminodiphenylamine (HC Blue No. 13), As red nitro dyes can be mentioned, for example:
1-amino-4-(2'-hydroxyethyl)amino-2-nitrobenzene (HC Red No. 7),
1-hydroxy-2-amino-4,6-dinitrobenzene,
4-amino-2-nitrodiphenylamine (HC Red No. 1),
1-amino-2-nitro-4-bis (2'-hydroxyethyl)aminobenzene hydrochloride (HC Red No. 13),
1-amino-2-nitro-4-(2'-hydroxyethyl)amino-5-chlorobenzene,
1-(2'-hydroxyethyl)amino-2-nitroaminobenzene (HC Red No. 3),
1-hydroxy-3-nitroaminobenzene,
1-hydroxy-3-nitro-4-(2'-hydroxyethylamino)benzene,
1-(2'-aminoethyl)amino-2-nitro-4-(2'-hydroxyethoxy)benzene (HC Orange No. 2),
3-nitro-4-(2'-hydroxyethyl)aminophenyl glyceryl ether (HC Orange No. 3),
1-amino-5-chloro-4-(2',3'dihydroxypropyl)amino-2-nitrobenzene (Red No. 10),
1,4-bis[(2',3'-dihydroxypropyl)amino]-5-chloro-2-nitrobenzene (HC Red No. 11),
1-hydroxy-2-(2'-hydroxyethyl)amino-4,6-dinitrobenzene,
3-nitro-4-ethylaminobenzoic acid,
4-amino-2-nitrodiphenylamino-2-carboxylic acid,
2-chloro-6-ethylamino-4-nitrophenol,
2-amino-6-chloro-4-nitrophenol,
1-hydroxy-3-nitro-4-(3'-hydroxypropylamino)benzene,
2,5-diamino-6-nitropyridine,
1,2,3,4-tetrahydro-6-nitroquinoxaline,
7-amino-3,4-dihydro-6-nitro-2H-1,4-benzoxazine (HC Red 14).

As yellow nitro dyes can be mentioned, for example:
1-amino-2-(2'-hydroxyethyl)amino-5-nitrobenzene (HC Yellow No. 5),
1-(2'-hydroxyethoxy)-2-(2"-hydroxyethyl)amino-5-nitrobenzene (HC Yellow No. 4),
1-(2'-hydroxyethyl)amino-2-nitrobenzene (HC Yellow No. 2),
1-methoxy-2-(2'-hydroxyethyl)amino-5-nitrobenzene,
1-hydroxy-2-amino-3-nitrobenzene,
1-amino-2-methyl-6-nitrobenzene,
1-(2'-hydroxyethyl)oxy-3-methylamino-4-nitrobenzene,
1-methylamino-2-nitro-5-(2',3'-dihydroxypropyl)oxybenzene,
1-(2'-hydroxyethyl)amino-2-hydroxy-4-nitrobenzene (HC Yellow No. 11),
1-methoxy-3-(2'-aminoethyl)amino-4-nitrobenzene hydrochloride (HC Yellow No. 9),
1-2'-ureidoethyl)amino-4-nitrobenzene,
4-(2',3'-dihydroxypropyl)amino-3-nitrotrifluoromethylbenzene (HC Yellow No. 6),
2,4-bis-[N-(2'-hydroxyethyl)amino]-5-chloronitrobenzene (HC Yellow No. 10),
4-(2'-hydroxyethyl)amino-3-nitromethylbenzene,
4-(2'-hydroxyethyl)amino-3-nitrochlorobenzene (HC Yellow No. 12),
4-(2'-hydroxyethyl)amino-3-nitrofluoromethylbenzene (HC Yellow No. 13),
4-(2'-hydroxyethyl)amino-3-nitrobenzonitrile (HC Yellow No. 14),
4-(2'-hydroxyethyl)amino-3-nitrobenzamide (HC Yellow No. 15).

As azo dyes can be mentioned, for example:
1-(4'-nitrophenylazo)-2-methyl-4-bis-(2'-hydroxyethyl)aminobenzene,
1-(3'-nitro-4-amino)phenylazo-2-hydroxy-7-trimethylammoniumnaphthalene chloride
1-(2'-hydroxy-4'-sulfo-6'-nitro)naphthylazo-2-hydroxynaphthalene, CI 15,700
1-(4'-aminophenylazo)-2-methyl-4-bis-[(2-hydroxyethyl)amino]benzene,
5-(4'dimethylaminophenylazo)-1,4-dimethyltriazonium chloride,
1-(2'-methoxyphenylazo)-2-hydroxy-7-trimethylammoniumnaphthalene chloride,
1-(4'-aminophenylazo)-2-hydroxy-7-trimethylammoniumnaphthalene,
4-(3'-trimethylammoniumphenylazo)-N-phenyl-3-methyl-5-pyrazolone,
4-hydroxy-3-[(4'-sulfo-1'-naphthyl)azo]-1-naphthalenesulfonic acid,
1-(4'-sulfophenylazo)-2-hydroxynaphthalene,
1-(4'-sulfophenylazo)-2-hydroxy-6-sulfonaphthalene, CI 15,985,
4-amino-[4'-bis-(2''-hydroxyethyl)amino]azobenzene,
4-amino[4'-bis-(2''-hydroxyethyl)amino]-2'-methylazobenzene,
3-(2',6'-diaminopyridyl-3'-azo)pyridine,
7-phenylazo-1-amino-3,6-disulfo-8-hydroxynaphthalene,
5-acetylamino-4-hydroxy-3-[(2'-methylphenyl)azo]-2,7-naphthalenedisulfonic acid,
2-(2',4'-dimethylphenylazo)-6-(4''-sulfophenylazo)-1,3-dihydroxybenzene.

As quinone dyes can be mentioned, for example:
1,4-bis-(2',3'-dihydroxypropyl)aminoanthraquinone,
1-methylamino-4-(2'-hydroxyethyl)aminoanthraquinone
2-(2'-aminoethyl)aminoanthraquinone,
2-bromo-4,8-diamino-6-(3'-trimethylammonium)phenylamino-1,5-naphthoquinone,
1-(2'-sulfo-4'-methylphenyl)amino-4-hydroxyanthraquinone,
1,4-diaminoanthraquinone,
1-amino-2-sulfo-4-cyclohexylaminoanthraquinone,
1-aminopropylaminoanthraquinone,
1,4-diamino-2-methoxyanthraquinone,
1,4-bis-(2-hydroxyethyl)amino-5,8-dihydroxyanthraquinone.

As triphenylmethane dyes can be mentioned, for example:
4',4'',4'''-triamino-3-methyltriphenylcarbonium chloride,
bis-(4,4-diethylaminophenyl)-4'-ethylaminonaphthylcarbonium chloride,
bis-(4,4-dimethylaminophenyl)-4'-phenylaminonaphthylcarbonium chloride, Basic Blue 26, CI 44,045, and
4,4-bis-(N-ethyl-3-sulfobenzyl)amino-2''-sulfofuchsonium.

As acid dyes can be mentioned, for example:
1-(4'-sulfophenylazo)-2-hydroxy-6-sulfonaphthalene, CI 15,985,
1-(2'-hydroxy-4'-sulfo-6'-nitro)naphthylazo-2-hydroxynaphthalene, CI 15,700,
2,4-dinitro-1-naphthol-7-sulfonic acid disodium salt (Acid Yellow 1; CI 10,316),
2-(2'-quinolyl)-1H-indene-1,3(2H)-dione monodisulfonic acid disodium salt (Acid Yellow 3; CI 47,005),
4,5-dihydro-5-oxo-1-(4'-sulfophenyl)-4-[(4''-sulfophenyl)azo]-1H-pyrazole-3-carbox trisodium salt (Acid Yellow 23; CI 19,140),
3',6'-dihydroxyspiro[isobenzofuran-1 (3H), 9'(9H)-xanthene]-3-one (Acid Yellow 73; CI 45,350:1),
5-[2',4'-(dinitrophenyl)amino]-2-(phenylamino)benzenesulfonic acid sodium salt (Acid Orange 3; CI 10,385),
4-[(2',4'-dihydroxyphenyl)azo]benzenesulfonic acid sodium salt (Acid Orange 6; 14,270),
4-[2'-hydroxy-1'-naphthyl)azo]benzenesulfonic acid sodium salt (Acid Orange 7, CI 15,510
4-[[3'-[(2'',4''-dimethylphenyl)azo]-2',4'-dihydroxyphenyl]azo]benzenesulfonic acid sodium salt (Acid Orange 24; CI 20,170),
4-hydroxy-3-[(4'-sulfo-1'-naphthyl)azo]-1-naphthalenesulfonic acid disodium salt (Acid Red 14; CI 14,720;
7-hydroxy-8-[(4'-sulfo-1'-naphthyl)azo-1,3-naphthalenedisulfonic acid trisodium salt (Acid Red 18; CI 16,285),
3-hydroxy-4-[(4'-sulfo-1'-naphthyl)azo]-2,7-naphthalenedisulfonic acid trisodium salt (Acid Red 27, CI 16,185);
5-amino-4-hydroxy-3-phenylazo-2,7-naphthalene disulfonic acid disodium salt (Acid Red 33, CI 17,200),
5-(acetylamino)-4-hydroxy-3-[(2'-methylphenyl)azo]-2,7-naphthalenedisulfonic acid disodium salt (Acid Red 35, CI 18,065),
3',6'dihydroxy-2',4',5',7'-tetraiodospiro-[isobenzofuran-1 (3H), 9'(9H)-xanthen]-3-one disodium salt (Acid Red 51, CI 45,430),
3,6-bis-(diethylamino)-9-(2',4'disulfophenyl)xanthylium hydroxide sodium salt (Acid Red 52, CI 45,100).
7-hydroxy-8-{[(4'-phenylazo)phenyl]azo}-1,3-naphthalenedisulfonic acid disodium salt (Acid Red 73, CI 27,290),
2',4',5',7'-tetrabromo-3',6'dihydroxyspiro-[isobenzofuran-1 (3H), 9'(9H)-xanthen]-3-one disodium salt (Acid Red 87, CI 45,380),
2',4',5',7'-tetrabromo-4,5,6,7-tetrachloro-3',6'dihydroxyspiro-[isobenzofuran-1(3H),9' (9H)-xanthen]-3-one disodium salt (Acid Red 92, CI 45,410),
3',6'-dihydroxy-4',5'-diiodospiro-[isobenzofuran-1(3H), 9'(9H)-xanthen]-3-one sodium (Acid Red 95, CI 45,425),
Acid Red 195, Acid Blue 9 (CI 42,090),
2,2'-[(9,10-dihydro-9,10-dioxo-1,4-anthracenediyl)diimino]-bis-(5-methylbenzenesulfonic acid disodium salt (Acid Green 25, CI 61,570),
N-{4-[(4'-dimethylamino)phenyl]-(2''-hydroxy-3'',6''-disulfo-1''-naphthyl)methylene}-2,5-cyclohexadien-1-ylidene-N-methylmethanaminium hydroxide (Acid Green 50, CI 44,090),
N-{4-[(4'-diethylamino)phenyl]-(2'',4''-disulfophenyl)methylene-]2,5-cyclohexadien-1-ylidene}-N-ethylethanaminium hydroxide sodium salt (Acid Blue 1, CI 42,045),
N-{4-[(4'-diethylamino)phenyl]-(5''-hydroxy-2'',4''-disulfophenyl)methylene-2,5-cyclohexadien-1-ylidene}-N-ethylethanaminium hydroxide calcium salt (Acid Blue 3, CI 42,051),
1-amino-4-(cyclohexylamino)-9,10-dihydro-9,10-dioxo-2-anthracenesulfonic acid sodium salt (Acid Blue 62, CI 62,045),
2-(1',3'-dihydro-3'-oxo-5'-sulfo-2'H-indol-2'-ylidene)-2,3-dihydro-3-oxo-1H-indole-5-sulfonic acid disodium salt (Acid Blue 74, CI 73,015),
9-(2'-carboxyphenyl)-3-[(2''-methylphenyl)amino]-6-[(2'''-methyl-4'''-sulfophenyl)amino]-xanthylium hydroxide sodium salt (Acid Violet 9, CI 45,190),
2-[(9',10'-dihydro-4'-hydroxy-9',10'-dioxo-1'-anthracenyl)amino]-5-methylbenzenesulfonic acid sodium salt (Acid Violet 43, CI 60,730),
3,3'-[sulfonyl-bis-(2-nitro-4'-phenylene)imino]-bis-[6-phenylamino)benzenesulfonic acid disodium salt (Acid Brown 13, CI 10,410),
4-amino-5-hydroxy-3-[(4'-nitrophenyl)azo]-6-(phenylazo)-2,7-naphthalenedisulfonic acid disodium salt (Acid Black 1, CI 20,470),
3-hydroxy-4-[(2'-hydroxy-1'-naphthyl)azo]-7-nitro-1-naphthalenesulfonic acid sodium salt (Acid Black 52, CI 15,711),
3-[(2,4-dimethyl-5-sulfophenyl)azo]-4-hydroxy-1-naphthalenesulfonic acid (Ponceau SX, CI 14,700).

As basic dyes can be mentioned, for example;
bis-4,4-dimethylaminophenyl)-4'-phenylaminonaphthylcarbonium chloride (Basic Blue 26, CI 44,045),
N-4-[[4'-(diethylamino)phenyl]-[4"-(ethylamino)-1"-naphthyl]methylene]-2,5-cyclohexadien-1-ylidene]-N-ethylethanammonium chloride (Basic Blue 7, CI 42,595),
4-[(4'-aminophenyl)-(4'-imino-2',5'cyclohexadien-1'-ylidene)methyl]-2-methylaminobenzene hydrochloride (Basic Violet 14, CI 42,510),
4-(acetylamino)-5-hydroxy-6-{[7'-sulfo-4'-[(4"-sulfophenyl)azo]-1'-naphthyl]azo}-1,7-naphthalenedisulfonic acid tetrasodium salt (Brilliant Black 1, CI 28,440),
{[8-(p-aminophenyl)azo]-7-hydroxy-2-naphthyl}trimethylammonium chloride (Basic Brown 16, CI 12,250),
{8-[(4'-amino-2'-nitrophenyl)azo]-7-hydroxy-2-naphthyl}trimethylammonium chloride (Basic Brown 17, 12,251),
7-hydroxy-8-[(2'-methoxyphenyl)azo]-N,N,N-trimethyl-2-naphthylammonium chloride (Basic Red 76, CI 12,245),
3-[(4'-amino-6'-bromo-5',8'-dihydro-1'-hydroxy-8'-imino-5'-oxo-2'-naphthyl)amino]-N,N,N-trimethylammonium chloride (Basic Blue 99, CI 56,059),
4-(3'-trimethylammoniumphenylazo)-N-phenyl-3-methyl-5-pyrazolone (Basic Yellow 57, CI 12,729).

The amounts of dyeing or coloring effector molecules, particularly hair dyes and preferably direct hair dyes, depend on the amounts known by those skilled in the art to be used for dyeing hair. Said amounts can range from a total of 0.001 to 10.0 wt. % and particularly from 0.001 to 5.0 wt. %, based on the total amount of the cosmetic agent.

The first component, which can be referred to as the peptidic linker molecule, comprises short-chain peptides that preferably are in the form of 2-mers to 30-mers, particularly 3-mers to 15-mers and more particularly 6-mers to 12-mers.

Preferred are peptides containing amino acid derivatives with a free amino, hydroxy or sulfonyl group, for example the derivatives of 3-aminoalanine, ornithine, lysine, serine, threonine, cysteine and homocysteine. Suitable are, for example, the following peptides:

```
AKKNR KTDND DS, DDDDE SEHHA KT, DDDE EEE, DDDEE
EDQKR SKKHR, DDDEE HHHR, DDDEE SEDES EEQ, DDEED
EDPTK ARKT, DDEEE EEDE, DDEEE RRHKK, DDEES EE,
DDERH HK, DDEHR K, DDETD DDSEP, DEDDE EETDN TSDNT,
DEEDD EQKHK ATRT, DEEDE ENKHH T, DEEDE TDDDE DNST,
DEEEH HHH, DEETE DDKSR KQN, DEETK SHTSA DESS,
DEKHH DKEE, DEKRT PQDTT LNQST, DETTQ TDKEE, EDDDS
EPHHR SKQ, EDEED ENPT DES, EDDEE E, EEDDE EEE,
EEDDE DDQHR NQ, EEDDP KKHH, EEDDS KRR, EEDED EDPKQ
HLLRN, EEDEE D, EEDEE SHHHK EEDSR RR, EEEDD EDDD,
EEEDD NDQEE D, EEEDD TPEEE KEESK, EEEDE DD, EEEEE
DSEDD, EEERK K, ESDED DDETQ PSTNT, ESEE EDPEE DE,
HHKKH RTEED E, HHKRR KPESE EETS, HHKSR RRRHQ,
HHRKE EE, HHRKK HRT, HHRKK K, HKKKE DDDD, HKRRH
RRQKK QKS, HRKKR KKRPE EDDER, HTSDK EH, KHHRK
RRDED TEEQ, KHHRK RRRK, KHSSS TTNEE EEQ, KKHDE DS,
KKHDD E, KKHHT HTKRR N, KKKHR SKSDD DDQ, KKKKR
EEDDE, KKKKR KKHKN NS, KKKN HSKHH KSS, KKKRR HS,
KKRTT HHNEE EN, KRHHK RRHKD TDEEN, KRRHH R, KRRRH,
KKKTK TSAK, KRTSN QPEDE RTHSL, NEDD DESNE EQ,
NHHRD EHDEH S, RKKHE NDQ, RKKHR HREDE DEEDQ, RKKSE
EEN, RRHHD DEE, RRKEE D, RRKKH HH, RRRHH HPEED
EDS, RRRHH KPRRA KH, RRRHH PRRK, RRTKK SHH, RTHHH
DQEEE, SEETS SQTHHK ATQ, SHEDD H, SHEHH TED, SHHKK
KHHH KTKA, SHKKR KSRRH K, SSKKT QTRRN KS, SSKKT
HQNST AT, SRRRK KHHSH, TDDDD EPSED T, TDDE DDEDD
TDPN, TEEDS DPKKK Q, TEKHD EKDD, TGGGH KPEED S,
THHES DK, THHRR EEED, TKEKD H, TTDEN ETTED, TSEES
HSADE T, TSKHH RPTSS EKTS.
```

To the agent of the invention may be added other substances, auxiliary agents and additives not attached to the peptidic linker, for example those commonly used for cosmetic products in general. Such materials include, for example, thickeners (for example clays, starches, polyacrylic acid and the derivatives thereof, cellulose derivatives or alginates), further hair and skin care materials (such as sugars, proteins, lanolin derivatives, vitamins or provitamins, e.g. biotin vitamin C, tocopherol or D-panthenol), antigrease agents, inorganic or organic acids (for example lactic acid, citric acid, glycolic acid or phosphoric acid), preservatives (for example para-hydroxybenzoate esters), nonaqueous solvents, antioxidants (for example tocopherols or the esters thereof), dyes and fragrances or perfumes, UV light-absorbing inorganic particles or pigments or micropigments, particularly metal compounds or semimetallic compounds in ionic, nonionic or oxidized form. The pigments can be in this form either individually or in admixture or as individual mixed oxides or mixtures thereof, including mixtures of mixed oxides and pure oxides. Examples are the titanium oxides (for example $TiO_2$), zinc oxides (for example ZnO), aluminum oxides (for example $Al_2O_3$), iron oxides (for example $Fe_2O_3$), manganese oxides (for example MnO), silicon oxides (for example $SiO_2$), silicates, cerium oxide, zirconium oxides (for example $ZrO_2$), barium sulfate ($BaSO_4$) or mixtures thereof. Suitable pigments or micropigments are commercially available. An example is Hombitec® L5 (INCI name: titanium dioxide) supplied by Merck.

Basically, those skilled in the art know which additives, auxiliary agents and carriers are used in hair and skin cosmetics so that the following statements are only of an exemplary nature and are intended only for further explanation of the present invention. Moreover, the reader is referred to the abundant literature describing the general composition of cosmetic preparations and which is well known to those skilled in the art.

The additives, auxiliary agents and carriers can be used in the usual amounts known to those skilled in the art and can be incorporated by methods in themselves known.

Before application, the first component, namely the peptidic linker, and the second component, namely the effector molecule, are linked to each other forming the high-affinity cosmetic agent of the invention, the finished commercial product possibly containing other common constituents, auxiliary agents and carriers.

The cosmetic agents of the invention can be in the form of different formulations known for cosmetic skin and hair products. For example, they can be in the form of shampoos, lotions, rinses, dispersions, emulsions, gels, cream gels, creams, suspensions, sprays, aerosols or foams.

EXAMPLES

The present invention will now be explained in greater detail by means of a dye as the effector molecule.

Example 1

Preparation of 5-((4-((5-amino-5-carboxypentyl)amino)-6-hydroxy-1,3,5-triazin-2-yl)amino)-4-hydroxy-3-(phenylazo)-2,7-naphthalenedisulfonic acid disodium salt (formula III)

Step 1

6.15 g (10 mmol) of Reactive Red 2 (based on 100% pure dye) and 2.0 g (11 mmol) of D,L-lysine hydrochloride were dissolved in 30 mL of water, and the pH was adjusted to 9-9.5 with 30% sodium hydroxide. The solution was then heated to 40° C. and stirred 6 hours while keeping the pH and temperature constant. The mixture was cooled to room temperature, and 5-((4-((5-amino-5-carboxypentyl)amino)-6-chloro-1,3,5-triazin-2-yl)amino)-4-hydroxy-3-(phenylazo)-2,7-naphthalenedisulfonic acid disodium salt was made to precipitate by addition of methanol in an amount commensurate with the crystallization.

Step 2

The moist product from Step 1 was taken up in 20 mL of water, 20 mL of 30% sodium hydroxide solution was added, and the reaction mixture was heated to 90° C. After 6 hours, the mixture was cooled, carefully acidified to pH 4.5 with acetic acid, and 5-((4-((5-amino-5-carboxypentyl)amino)-6-hydroxy-1,3,5-triazin-2-yl)amino)-4-hydroxy-3-(phenylazo)-2,7-naphthalenedisulfonic acid disodium salt, (formula III) was made to precipitate by addition of methanol (about 40 mL). Filtering and drying gave 5.8 g of dye in the form of a red powder. The $\lambda_{max}$ value of the dye in water was 544 nm.

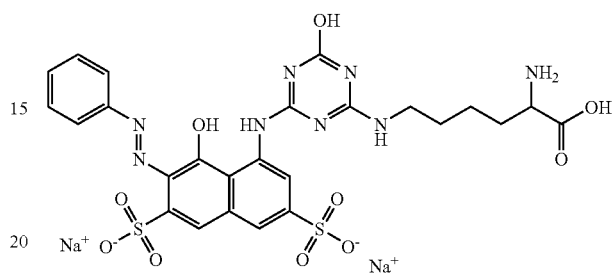

III

Example 2

Preparation of 1-amino-4-((3-((2-(((5S)-5-amino-5-carboxypentyl)amino)ethyl)sulfonyl) -phenyl)amino-9,10-dioxo-9,10-dihydro-2-anthracenesulfonic acid sodium salt (formula V)

Step 1

6.26 g (10 mmol) of Reactive Blue 19 (based on 100% pure dye) and 2.7 g (11 mmol) of N(alpha)-BOC-L-lysine were dissolved in 30 mL of water, and the pH was adjusted to 9-9.5 with 30% sodium hydroxide. The solution was then heated at 90° C. for 6 hours while keeping the pH constant at 4.5 by addition of sodium hydroxide solution. The reaction product was then made to precipitate by addition of methanol (about 40 mL). Filtering and drying gave 5.4 g (71% of the theoretical) of 1-amino-4-((3-((2-(((5S)-5-(((1,1-dimethoxyethoxy)carbonyl)amino)-5-carboxypentyl)amino)ethyl)sulfonyl)phenyl)-amino-9,10-dioxo-9,10-dihydro-2-anthracenesulfonic acid sodium salt as a blue powder.

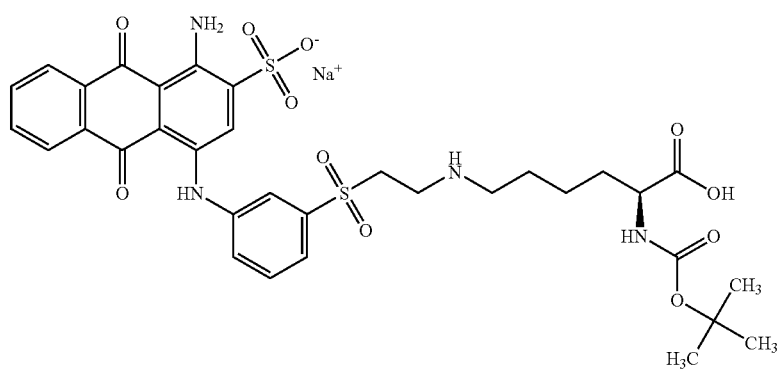

IV

Step 2

2.0 g (2.6 mmol) of the compound from Step 1 was stirred in 10 mL of hydrochloric acid (concentration: 1 mol/L) for 2 hours at room temperature. The dye was made to precipitate by addition of 20 mL of methanol. Filtering and drying gave 1.4 g (82% of the theoretical) of 1-amino-4-((3-((2-(((5S)-5-amino-5-carboxypentyl)amino)ethyl)sulfonyl) phenyl)amino)-9,10-dioxo-9,10-dihydro-2-anthracenesulfonic acid sodium salt as a blue powder. The $\lambda_{max}$ value of the dye in water was 598 nm.

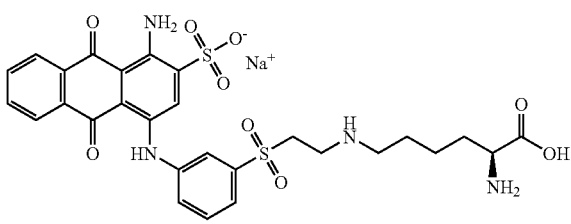

V

Example 3

Preparation of (2S)-2-amino-6-((2,4-dinitrophenyl) amino)hexanoic acid (N-6-(2,4-dinitrophenyl)-L-lysine)

Step 1

1.86 g (10 mmol) of 2,4-dinitrofluorobenzene and 2.7 g (10 mmol) of N(alpha)-BOC-L-lysine were heated in 30 mL of acetonitrile at 90° C. for 6 hours. The batch was cooled to room temperature, and the acetonitrile was distilled off. This gave 4.1 g (99% of the theoretical) of 6-((4-amino-2-nitrophenyl)amino-(2S)-2-(((1,1-dimethylmethoxy)carbonyl)amino)hexanoic acid (formula VI) as a bright yellow solid residue.

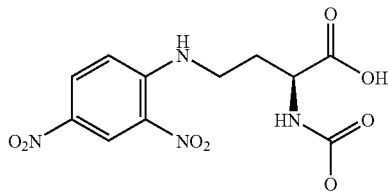

VI

Step 2

3.2 g (7.8 mmol) of the compound from Step 1 was stirred in 10 mL of hydrochloric acid in dioxane (concentration: 3 mol/L) at room temperature for 3 hours. At the end of the reaction, the dye was made to precipitate by addition of 20 mL of diethyl ether. Filtering and drying gave 2.1 g (95% of the theoretical) of (2S)-2-amino-6-((2,4-dinitrophenyl) amino)hexanoic acid (N-6-(2,4-dinitrophenyl)-L-lysine) (formula VII) as a bright-yellow powder.

The lambda$_{max}$ value of the dye in ethanol/water (1:1) was 412 nm.

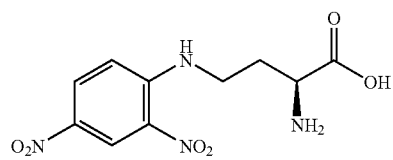

VII

SUMMARY

The present invention relates to a cosmetic agent consisting essentially of a peptidic linker and at least one cosmetic agent covalently linked therewith.

The invention claimed is:

1. A cosmetic composition for cosmetically treating parts of a human or animal body, said parts comprising keratin-containing material, wherein said cosmetic composition comprises
    at least one cosmetically active compound, wherein said at least one cosmetically active compound comprises at least one organic cosmetic effector molecule and at least one peptidic linker covalently linked or bonded to said at least one organic cosmetic effector molecule, said at least one peptidic linker having binding specificity for said keratin-containing material or being able to act as a binding agent for binding to said keratin-containing material; and
    at least one cosmetic auxiliary ingredient selected from the group consisting of thickeners, vitamins, provitamins, antigrease agents, antioxidants, preservatives, perfumes and UV light-absorbing inorganic pigments;
    wherein said at least one organic cosmetic effector molecule has dyeing properties, cosmetic care-imparting properties, conditioning properties, protective properties, hardening properties, softening properties, repairing properties and/or reconstituting properties.

2. The cosmetic composition as defined in claim 1, wherein said at least one peptidic linker binds preferentially to damaged areas of hair of the animal or human body.

3. The cosmetic composition as defined in claim 1, wherein said at least one peptidic linker is a peptide with a chain length of from 2 to 30 amino acids.

4. The cosmetic composition as defined in claim 3, wherein said chain length is from 3 to 12 of said amino acids.

5. The cosmetic composition as defined in claim 1, wherein said at least one organic cosmetic effector molecule is selected from the group consisting of hair dyes, hair conditioners, combability improvers, surfactants, amidoamines, betaines, betaine esters, ester quats, silicone polyols, fatty alcohols, chitosan, humectants, springiness improvers, sugars and UV filters.

6. A cosmetic composition for cosmetically treating parts of a human or animal body, said parts comprising keratin-containing material, wherein said cosmetic composition comprises
    at least one cosmetically active compound, wherein said at least one cosmetically active compound comprises at least one organic cosmetic effector molecule and at least one peptidic linker covalently linked or bonded to said at least one organic cosmetic effector molecule, said at least one peptidic linker having binding specificity for said keratin-containing material or being able to act as a binding agent for binding to said keratin-containing material; and at least one cosmetic auxiliary ingredient selected from the group consisting of thickeners, vitamins, provitamins, antigrease agents, antioxidants, preservatives, perfumes and UV light-absorbing inorganic pigments;

wherein said at least one organic cosmetic effector molecule has dyeing properties, cosmetic care-imparting properties, conditioning properties, protective properties, hardening properties, softening properties, repairing properties and/or reconstituting properties;

wherein said at least one organic cosmetic effector molecule is at least one direct dye for dyeing hair and said at least one direct dye is selected from the group consisting of nitro dyes, azo dyes, quinine dyes, triphenylmethane dyes, acid dyes and basic dyes.

7. The cosmetic composition as defined in claim 1, wherein said at least one cosmetically active compound comprises different organic cosmetic effector molecules covalently bound to a single peptidic linker molecule.

8. The cosmetic composition as defined in claim 1, wherein said at least one cosmetically active compound comprises respective different peptidic linkers having different binding strengths for said keratin-containing material and corresponding different organic cosmetic effector molecules covalently bound to said respective different peptidic linkers.

9. The cosmetic composition as defined in claim 1, wherein said at least one cosmetically active compound comprises different peptidic linkers and said different peptidic linkers have different binding strengths for said keratin-containing material and different binding sites on said keratin-containing material.

10. A method of performing a cosmetic treatment of parts of a human or animal body, said parts comprising keratin-containing material, wherein said method comprises the steps of:
a) providing at least one cosmetically active compound, wherein said at least one cosmetically active compound comprises at least one organic cosmetic effector molecule and at least one peptidic linker covalently linked or bonded to said at least one organic cosmetic effector molecule, said at least one peptidic linker having binding specificity for said keratin-containing material; and
b) applying the at least one cosmetically active compound formed in step a) to said parts of said human or animal body that contain said keratin-containing material so as to perform said cosmetic treatment;
wherein said at least one organic cosmetic effector molecule has dyeing properties, care-imparting properties, conditioning properties, protective properties, hardening properties, softening properties, repairing properties and/or strengthening properties for said keratin-containing material.

11. The method as defined in claim 10, wherein said parts of said human or animal body consist of hair.

12. The method as defined in claim 11, wherein said at least one peptidic linker binds preferentially to damaged areas of said hair of the animal or human body.

13. A method of performing a cosmetic treatment of parts of a human or animal body, said parts comprising keratin-containing material, wherein said method comprises the steps of:
a) providing at least one cosmetically active compound, wherein said at least one cosmetically active compound comprises at least one organic cosmetic effector molecule and at least one peptidic linker covalently linked or bonded to said at least one organic cosmetic effector molecule, said at least one peptidic linker having binding specificity for said keratin-containing material; and
b) applying the at least one cosmetically active compound formed in step a) to said parts of said human or animal body that contain said keratin-containing material so as to perform said cosmetic treatment;
wherein said at least one organic cosmetic effector molecule has dyeing properties, care-imparting properties, conditioning properties, protective properties, hardening properties, softening properties, repairing properties and/or strengthening properties for said keratin-containing material; and wherein said at least one organic cosmetic effector molecule is at least one hair dye.

14. The method as defined in claim 13, wherein said at least one hair dye is a direct dye and said direct dye is selected from the group consisting of nitro dyes, azo dyes, quinine dyes, triphenylmethane dyes, acid dyes and basic dyes.

15. The method as defined in claim 10, wherein each of said at least one peptidic linker is a peptide with a chain length of from 2 to 30 amino acids.

16. The method as defined in claim 10, wherein said at least one organic cosmetic effector molecule is selected from the group consisting of dyes, hair conditioners, combability improvers, surfactants, amidoamines, betaines, betaine esters, ester quats, silicone polyols, fatty alcohols, chitosan, humectants, springiness improvers, sugars and UV filters.

17. The method as defined in claim 10, further comprising applying a cosmetic composition containing said at least one cosmetically active compound to said parts of said human or animal body, and wherein said cosmetic composition also includes at least one cosmetic auxiliary ingredient selected from the group consisting of thickeners, vitamins, provitamins, anti-grease agents, antioxidants, preservatives, perfumes and UV-light absorbing inorganic pigments.

18. The cosmetic composition as defined in claim 1, wherein said at least one peptidic linker is glycine or a glycine derivative of formula (I):

$$X\text{-}L\text{-}CH(NHR_S)\text{-}CO_2H \qquad (I),$$

wherein $R_S$ is H or a t-butoxycarbonyl group, L is an alkylene group or a phenylene group, and X denotes an amino group, a hydroxyl group, or a sulfonyl group.

19. The cosmetic composition as defined in claim 1, wherein said at least one peptidic linker is a peptide with a chain length of from 3 to 15 amino acids and said amino acids are selected from the group consisting of 3-aminoalanine, ornithine, lysine, serine, threonine, cysteine and homocysteine.

20. The method as defined in claim 10, wherein said at least one peptidic linker is glycine or a glycine derivative of formula (I):

$$X\text{-}L\text{-}CH(NHR_S)\text{-}CO_2H \qquad (I),$$

wherein $R_S$ is H or a t-butoxycarbonyl group, L is an alkylene group or a phenylene group, and X denotes an amino group, a hydroxyl group, or a sulfonyl group.

21. The method as defined in claim 10, wherein said at least one peptidic linker is a peptide with a chain length of from 3 to 15 amino acids and said amino acids are selected from the group consisting of 3-aminoalanine, ornithine, lysine, serine, threonine, cysteine and homocysteine.

* * * * *